US008639779B2

(12) United States Patent
Carnevale

(10) Patent No.: US 8,639,779 B2
(45) Date of Patent: Jan. 28, 2014

(54) REMOTE EXAM VIEWING SYSTEM

(76) Inventor: Matthew Carnevale, Medford, MA (US)

( * ) Notice: Subject to any disclaimer, the term of this patent is extended or adjusted under 35 U.S.C. 154(b) by 63 days.

(21) Appl. No.: 13/374,495

(22) Filed: Dec. 30, 2011

(65) Prior Publication Data

US 2013/0173750 A1 Jul. 4, 2013

(51) Int. Cl.
*G06F 15/16* (2006.01)
(52) U.S. Cl.
USPC .......................................... 709/219; 351/246
(58) Field of Classification Search
USPC ................................... 709/218, 219; 600/407
See application file for complete search history.

(56) References Cited

U.S. PATENT DOCUMENTS

| 8,094,909 B2* | 1/2012 | Maier et al. ................... 382/131 |
| 8,348,429 B2* | 1/2013 | Walsh et al. ................. 351/210 |
| 2002/0156650 A1* | 10/2002 | Klein et al. ....................... 705/2 |
| 2002/0186818 A1* | 12/2002 | Arnaud et al. ................ 378/165 |
| 2005/0251006 A1* | 11/2005 | Dellis ........................... 600/407 |
| 2006/0025670 A1* | 2/2006 | Kim et al. ..................... 600/407 |
| 2012/0065518 A1* | 3/2012 | Mangoubi et al. ............ 600/473 |

OTHER PUBLICATIONS

Garvin, Intraretinal Layer Segmentation of Macular Optical Coherence Tomography Images Using Optimal 3-D Graph Search, Oct. 2008, IEEE, pp. 1, 5(figure 12), and 6.*

* cited by examiner

*Primary Examiner* — Patrice Winder
*Assistant Examiner* — Eyob Hagos
(74) *Attorney, Agent, or Firm* — Robert K. Tendler

(57) ABSTRACT

An Internet-enabled software engine is provided on a global server to provide remote viewing and manipulation of ophthalmic exams, with the Internet-enabled software engine being an instantiation of the functionability of the OCT machine on which the exam is performed, and with the Internet-enabled software engine providing both remote viewing of OCT exams and manipulation of this data, thus to give a user the ability to view and manipulate the dense data sets associated with ophthalmic exams anywhere in the world with ease.

20 Claims, 16 Drawing Sheets

Convert Format Sub-Routines

OCT Patient Demographics Retrieval Service

OCT Patient Exam Retrieval Service

Internet/Mobile Viewer Application

REMOTE EXAM VIEWING SYSTEM

FIELD OF THE INVENTION

This invention relates to optical coherence tomography (OCT) and more particularly to a remote exam viewing system involving a web-enabled engine for ophthalmic exam review.

BACKGROUND OF THE INVENTION

As is well known ophthalmic devices such as OCT scanners generate large volumes of proprietary data that cannot be displayed on the web and require installation of expensive custom software on a computer in order to review the results of an exam and also to be able to exercise the OCT device to provide various segmentations or views of the data.

It is true that device manufacturers provide software to review or manipulate exam data, however, at significant cost and only operating on a local area network.

This is neither convenient nor helpful to most ophthalmologists who see patients in multiple exam rooms, in more than one office and in many cases see the same patients in multiple offices. Moreover, ophthalmologists have a need to consult with referring physicians to review patient exam data. Thus the need exists for a system that can extract raw data from ophthalmic OCT devices, upload the data to a server and provide the user with the ability to review and manipulate the exam data from any web-enabled computer with the same functionality and control as the ophthalmic device itself.

More particularly, optical coherence tomography devices are computer driven so that one can operate their software to view and quantify exam data so that an individual practitioner can do an analysis of the images on the device itself. One can measure retinal thickness and change over time and do so on three dimensional diametric scans that are remotely viewed on computers connected to the same local area network so that a person who is not in the examining room is able to do various types of analysis on the exams.

In order to accomplish such a goal, manufacturers have developed remote viewing software packages that need to be installed on each computer in order to run and have to be connected to a local area network, meaning the network that exists in the same office. Moreover, such a network is often times very crowded or segmented and no attempts are made to optimize speed or connection quality between the OCT device and the viewing computer. After software has been installed and each computer has been configured properly to communicate with the OCT device, a practitioner can go to the next exam room in the same office and pull up the exam data to view it.

Some systems are currently attempting to provide wide area network WAN access to ophthalmic OCT exams. However they are primitive in nature and are "image only" displays which are lower quality and limited representations of the raw data, and in many cases are simply scanned copies of printed paper reports. They import standard image file formats such as TIF, BMP, JPG and AVI; and they display them in a web page, which is highly inefficient and occupies far more storage space than necessary. However, OCT exams contain much more data than simple images and this limits the user's ability to manipulate or analyze the exam.

As mentioned before, many manufacturers require custom software installation on each computer in order for the user to be able to use and view the images. The problem with this type of approach is that one has to have a separate piece of software for each device, and for each manufacturer; and if one wants to view them simultaneously there is no common platform available. More particularly, there is no convenient way to review a patient exam record that incorporates exams performed on two different devices.

While recent attempts have been made to create some remote viewing functionality, these fail if a doctor has one office A and then across town there is an office B. This is because both offices are not on the same local network and one would need some sort of web-enabled remote viewing package such as Logmein or TightVNC.

The problem with remote viewing packages such as TightVNC, Logmein, and other remote viewing packages is that they provide very limited functionality and display of the data. Moreover, there are certain bottlenecks to the use of standard web-enabled viewers.

If one is simply interested in remote viewing and control via virtual control of a computer, if for instance a doctor is in Office A and wants to see an exam in Office B, he would have to make sure that no one else is using the device in Office B or else he would have to wait until the user finishes. Thus one of the problems remote viewing is multiple users.

The second problem with web-enabled remote viewers is the low quality of the images on the screen. The reason for this is that present remote viewing packages usable on the web use compression to speed up the transmission of the data in order to be able to see the changes on the screen. However, these compression techniques operate in color space due to the high color depth of graphics displays, and present a noticeable reduction in the quality of the transmitted images.

Finally, there is the question of latency. Remote viewing web-enabled programs to date repaint or refresh the screen when there is a change in any part of the data being displayed. Thus latency is very high when one is refreshing the screen and drawing images. This means that the practitioner has to wait for the screen to refresh, sometimes on the order of many seconds. As will be appreciated, the more one changes the screen the more data that has to be transmitted and therefore the slower the response of the program.

It will also be appreciated that not only is remote viewing desirable, remote manipulation of the data is also required. For instance as one wants to pick a particular segmentation, zoom in on some particular data, change a particular parameter in the basic program or in general remotely access the original device, currently there is no way in order to provide such a service.

In short, and as mentioned above, the current systems that are attempting to provide wide area network access to ophthalmic exams are either primitive, low resolution image only displays having little or no ability to manipulate and analyze an exam, or have high latency, poor image quality and introduce bottlenecks into clinic flow. As mentioned, existing systems require custom software installation on each computer, and those systems that utilize remote viewing and applications are problematic due to the lag time of transmitting the desktop images over the web. Moreover, the images that are produced are of poor quality due to compression. These systems also create a bottleneck because the user cannot review an exam while the device is in use by someone else.

SUMMARY OF INVENTION

In order to provide remote viewing and manipulation of ophthalmic OCT exams, a web-enabled software engine on a global server is utilized to collect, store, retrieve, view and manipulate these exams. The web-enabled engine is an instantiation or duplicate of the functionality that the OCT machine on which the exam was performed is able to provide.

Remote computers and devices can access this server to both view and manipulate the data in this server in real time with the look and feel of the OCT machine duplicated by the web-enabled engine to match that of the original OCT machine. Due to the bidirectional component of the engine, various types of data, such as patient demographics and existing OCT exams can also be sent back to the OCT machine, to eliminate data entry errors and allow further processing of existing exam data.

Exam data is extracted from each OCT device and in many cases this data is raw binary data. In the subject invention extracted data is securely uploaded to the server using a secure encrypted web-enabled client program. Thereafter the server can open the extracted data, convert and process it to web-capable formats in real time, and can serve the content to numerous web connections anywhere in the world upon request.

The user can then view and manipulate the extracted exam data using web-enabled devices such as a computer, an Ipad, an android tablet, an Iphone or other such device. The user can manipulate the exam with the exact same functionality as the ophthalmic device itself using the engine's custom designed web interface screens, that communicate with the server, download all the web available exam data, and provide similar screen controls and layouts as does the ophthalmic device itself. Note that the web interfaces are developed using web-enabled technology such as HTML 5, Microsoft Silverlight, ipad/iphone apps, android apps, and the like. Note further that both OCT and patient demographic data accessible to the server can be pushed back to the ophthalmic OCT device software, either through a client program or directly to the OCT device software if it supports such features, so that it can be processed on the original ophthalmic device.

Note for purposes of the subject invention the ophthalmic device referred to is an optical coherence tomography device which, interalia, outputs raw data in the form of core data components. Such core data components can include for instance scan location coordinates, which are the coordinates in the reference image that define the location of the OCT scan. Secondly, the core data may include a reference image which is a forward facing view of the eye surface in the image, either posterior or anterior. This can be generated by numerous methods such as SLO, LSLO, video camera, photograph, enface summation algorithms and the like. It is the purpose of the reference image to provide the user with a normal looking view so the user can see the locations of the OCT scans as they correlate to the surface of the eye.

Thirdly, a core data component is the OCT scan data itself. These are the OCT cross sectional scans that show the tissue layers of the segment of the eye being imaged, in one embodiment the retina.

The next core data components are the scale factors which are conversion factors that allow anatomical measurements to be made by counting pixels in the reference image and the OCT images.

Core data components of an exam from an OCT instrument can include segmentation data. This data is obtained from automatic image processing routines that analyze the OCT scans and outline various anatomic structures, such as the layers of the retina, the layers and surfaces of the cornea, the iris, the lens, the optic nerve head, etc. Note, each OCT device performs this type of an analysis and stores the results. The results can be extracted from the OCT device and sent to the server which stores and displays the segmented data on the remote viewing device. The routines that perform these analyses can also be incorporated into the client, server or even within the remote viewing device itself.

As will be seen, there are various types of segmentation, one of which is retina layer segmentation that allows the user to view layers of the retina that are the results of the analysis. Additionally, there is optic nerve segmentation in which the shape and cupping of the optic nerve is derived from the analysis that defines the shape and cupping of the optic nerve.

There is also anterior segmentation which is the result of analysis that defines the anterior surfaces of the eye, such as the iris, the posterior lens surface and the cornea.

Finally there is normative data. Many OCT device manufacturers have compiled normative databases that correlate the thickness results of the retina layer segmentation around the optic nerve to a database of a wide array of patient samplings to determine if the results are normal or suggestive of disease.

While the above are examples of various segmentations available from some OCT devices, every device has its unique variation of what they can detect and present. The subject system accommodates all of the variations and can provide quality visuals for common exam parameters regardless of machine differences, with the presentations for the subject system being customizable to various different manufacturers and the OCT devices.

Thus, in order to provide remote exam viewing and manipulation, the first step is extracting all the useful information that resides within the exam within the OCT device so that one can create that functionality within the web-enabled engine. Secondly, once that data is extracted, the subject invention provides means to transport it across the web securely to a server. Then after the exam resides in the server the system provides a web service that will convert the data and process it into a web format so that it can be transmitted worldwide using a communication scheme involving web browsers or web-enabled applications that are able to display the required exam data and offer the functionality of the OCT device itself.

Rather than using remote control software, the subject system has much better resolution and much lower latency because in the subject system one is not operating the OCT device itself and transmitting a screen every time it updates.

In the subject system one is actually copying the data, namely the exam, off the OCT machine onto a server and then transmitting that data in its full quality to the web-enabled application that is trying to view the exam.

It will be appreciated most internet connections provide sufficient bandwidths to provide real time viewing and manipulation. Presently the average connection speed is more than adequate so that transmission speeds from 256 Kb/sec to 40 Mb/sec are clearly sufficient for the subject processes. Note also that one can apply various compression algorithms to the images to provide either a lossy or lossless image format, such as jpeg or jpeg2000 to balance image purity and transmission speed to fine-tune the performance based on the quality of the connection.

In the subject system the type of compression utilized does not resort to compressing a full color image, but rather is a compression scheme that is targeted towards the monochromatic data that the OCT machines output. When dealing with monochromatic data one is dealing with a much smaller data set, whereas, with color one has three times the amount of information.

Note also that the subject system is bidirectional so that bidirectional communication is established between the OCT device, the server, and the remote viewing application.

In operation, if one is looking at the OCT scans on a reference image, all the information is transferred when the exam is opened and one can simply scroll through this data and perform the viewing functionality without requiring any more data. Alternatively, the subject system can be implemented to transfer the OCT scans one at a time, as they are accessed by the user.

However, if the practitioner wishes to see some segmentation data or some thickness contour maps that are generated on the server and then transmitted to the web-enabled viewer program, the viewer permits the user to control what is displayed, for instance a thickness contour map. The user may also be provided with an icon to click on that requests the information from the server. Note that the server generates the requested information by processing image and or numerical data and sending it to the remote viewing device that the data is to be displayed on. It should also be noted that the routines that generate this information can alternatively be implemented into several other parts of the engine, such as in the client, during the importing to the server, during the exporting to the viewer, or even in the viewing application itself.

It will be noted that the subject system can handle a wide variety of machines due the fact that there is a necessary commonality between the data that the practitioners want to view and manipulate and that which is available from an OCT machine.

The core data captures this commonality which permits viewing of all types of data including reference images and location as to where on the eye the OCT data corresponds. There is also volume block capability or a different series of protocols so that the practitioner can correlate the OCT scan to the reference image.

The OCT output may be a B-scan or series of B-scans, with these B-scans corresponding to the positions marked on the retina. Note that B-scans are very common across all OCT platforms.

As mentioned above in addition to the B-scans, segmentation permits viewing and measuring of different layers of the retina. For instance OCT devices provide some sort of analysis which essentially tells the practitioner where the top of the retina is, where the bottom is, and as many layers as can be distinguished therebetween. These machines can also display individual layers on the screen and can present a B-scan that is selected along with a graphic display that presents to the practitioner the thickness of the layers so that the practitioner can see if the retina is a normal, healthy thickness or if it is thinning, thickening, or has some pathology in it.

Another way to provide remote viewing of the OCT scan is to actually store the data extracted from the device in the same format that is used by the OCT device itself The system therefore stores the data in a raw data file format that duplicates the raw data format file of the OCT device, with this raw data file in the server used to create the remote images.

The purpose of the subject system is to duplicate what practitioners are used to seeing on a given device and to do so on a remote web-enabled device, as well as giving the practitioner the same controls and the same data as the original machine.

Moreover, the subject system permits remote comparison of exams taken at different times. This is possible because there is a common database and imaging platform. For instance, the first item that the practitioner may see when he walks into an exam room on a remote viewing station is a list of patients. The practitioner can then select a particular patient and get a corresponding list of every imaging modality that the patient has had, namely their whole imaging history.

The practitioner then can select for instance two different OCT exam records and the system will tell the doctor whether one exam is performed on for instance a Heidelberg Spectral machine or on for instance on a Zeiss Cirrus machine. It is important to note that the subject system enables to practitioner to select each exam and view them through the same piece of software, namely that which is communicating with the server. It also permits the practitioner to align one exam with the other so that one can have a comparative multiview of OCT data for the exact same region of the eye. The multiview can for instance be one window having the current exam on the top and a previous exam on the bottom so that the practitioner can compare the scans. The difference between the two exams can be presented in multiple ways, such as a topographic display showing the change in thickness over time.

One can also compare thickness graphs from various machines and various exams by plotting the difference between the segmentation layers to end up with a chart or a plot in millimeters.

So thus, while the data may be acquired from different devices and at different times the measurements are the same so that all the data corresponds.

In summary the major advantage of the subject system is to give the user the ability to review and manipulate the dense data sets anywhere in the world with ease. One can be at a conference or in a hotel room and can even present the data and manipulate the data from an ipad. One can view and manipulate the data from home or another office.

Another advantage for instance is the ability to present the data to a general ophthalmologist who is referring a patient so a specialist can perform the exam and actually allow the general ophthalmologist the ability to log onto the system and review the exam with the specialist without the need for expensive specialized software. This introduces a telemedicine component in which doctors can share the exam data for a common patient.

Moreover the practitioner can control how the data is presented to him regardless of the manufacturer of the OCT device. If for instance a practitioner prefers the look and feel of a particular OCT machine they can select the presentation they like regardless of the machine on which the exam was actually performed. Thus, one can take the Zeiss Cirrus data to make its presentation look exactly like the Heidelberg output simply by remote commands.

Because there is no specialized proprietary software for each machine the expense of the subject system is much less than those employing a local area network and specialized software for each computer. Also there are no multiuser bottlenecks because of the utilization of the web and its multiuser capabilities.

BRIEF DESCRIPTION OF THE DRAWINGS

These and other features of the subject invention will be better understood in connection with the Detailed Description in conjunction with the Drawings, of which.

DETAILED DESCRIPTION

Figure 1:
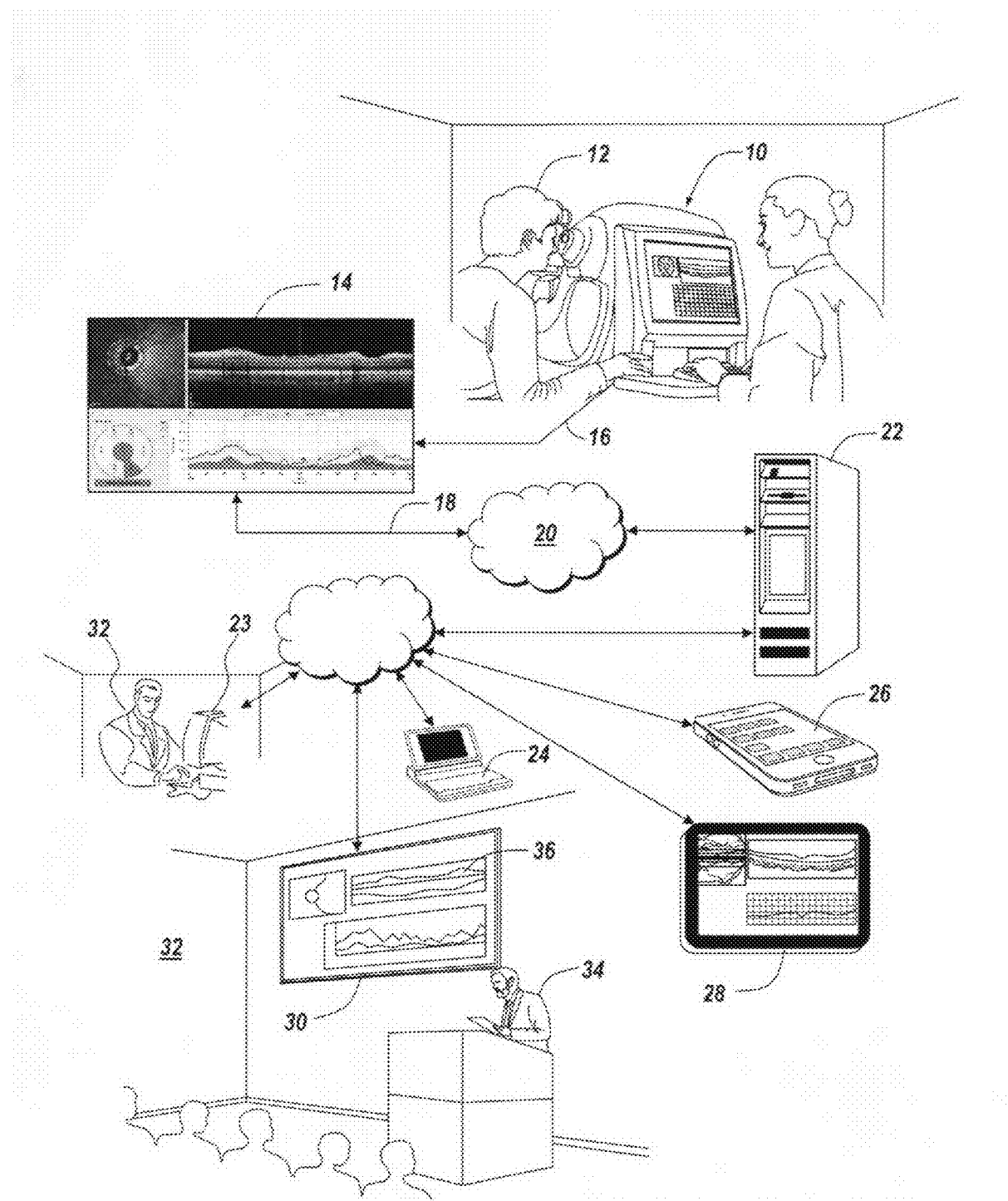
FIG. 1 is a diagrammatic illustration of the utilization of a web-enabled server to capture the information from an OCT device and to distribute it to various worldwide locations at which the results of the OCT scan can be viewed and manipulated.

Referring now to FIG. 1, an OCT device 10 is utilized to scan the eye of an individual 12, with OCT 10 outputting on a display 14 the results of the OCT scan. The raw data generated by the device is outputted at 16 and is then coupled via connection 18 to the web 20 where it is coupled to a server 22 that takes the raw data, stores it and stands ready to receive download requests from web-enabled devices such as a computer 23 at a separate office, a laptop 24, a Smart phone 26, a tablet 28 or a computer driven wall display 30 in a lecture room 32.

It is the purpose of the subject invention to enable a user 34 at a conference to be able to access the stored data in server 22 so as to be able to view and manipulate the results of an OCT exam, here shown at 36, which corresponds to the data shown in display 14 that is the direct output of OCT device 10.

Figure 2:
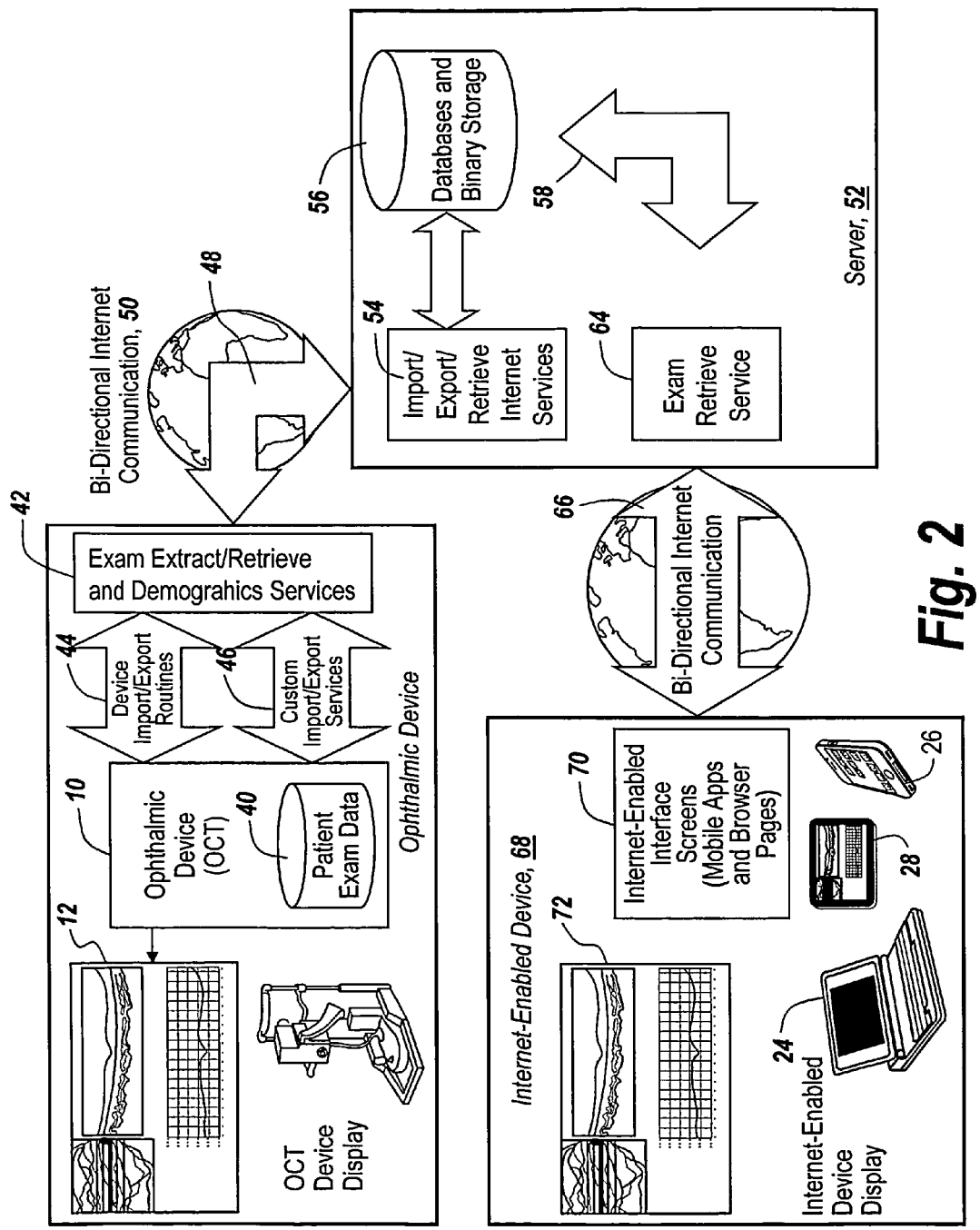
FIG. 2 is a diagrammatic illustration of the flow of information from an ophthalmic device via bidirectional web communication through a web server and thence to a web-enabled device.

It is also the purpose of the subject invention to provide user 34 with an input device for selecting what data in server 22 he or she wishes to see presented on his or her screen. This provides the remote user with the ability to access the results of an OCT scan in real time and to be able to control and manipulate what it is that he or she is seeing on his or her screen. It is the purpose of the subject system to be able to provide high quality OCT images and data on the remote screen in real time and to be able to manipulate the data in real time so as to provide real time renderings at the remote location, with the renderings being of extremely high resolution and quality. These renderings are also provided in real time due to the fact that the entire screen is not being transmitted across the web from another machine. Referring to FIG. 2 the OCT device 10 of FIG. 1 is shown having a display 12 in which the device 10 is populated with patient exam data 40. This exam data is presented on display 12, but more importantly is routed to a communication web service 42 in which OCT device 10 imports and exports data through a routine 44 that is incorporated into the OCT device software which passes the data in one embodiment as a native output format from device 10. There is also an ability to utilize custom developed import/export routines 46 to extract native raw data in the absence of routine 44 so that the full functionality of the ophthalmic device may be exercised.

The output of the communication web service 42 is connected in a bidirectional manner as illustrated by double ended arrow 48 over the web 50 to a web server 52 which includes import/export web services 54 that couple the incoming data to a database and binary storage unit 56 which is coupled in a bidirectional fashion as illustrated by arrow 58 to web services 64, which then processes and converts the data as necessary and distributes the output of the web server as illustrated by bidirectional web communication arrow 66 to a web enabled device 68 that may be any one of the devices 24, 26 and 28 described in connection with FIG. 1.

Each of the web enabled devices has a web enabled interface screen 70 including mobile applications and browser pages. The result is that the web enabled device is able to display on a screen 72 a duplicate of what is displayed by the ophthalmic device itself, namely screen 12. Thus in one embodiment the high quality data displayed at screen 12 is available at the web enabled device in exactly the same quality because it is pushed from a web enabled server that contains all of the OCT data.

Likewise when a user wishes to query the web server, the rendering of the result of the query is done in real time without any latency due to the fact that the screen need not be retransmitted over the web with every command. Also as noted before, since monochromatic images are output from the ophthalmic device and transmitted across the web, compressing color snapshots of the entire desktop screen is avoided.

Figure 3:
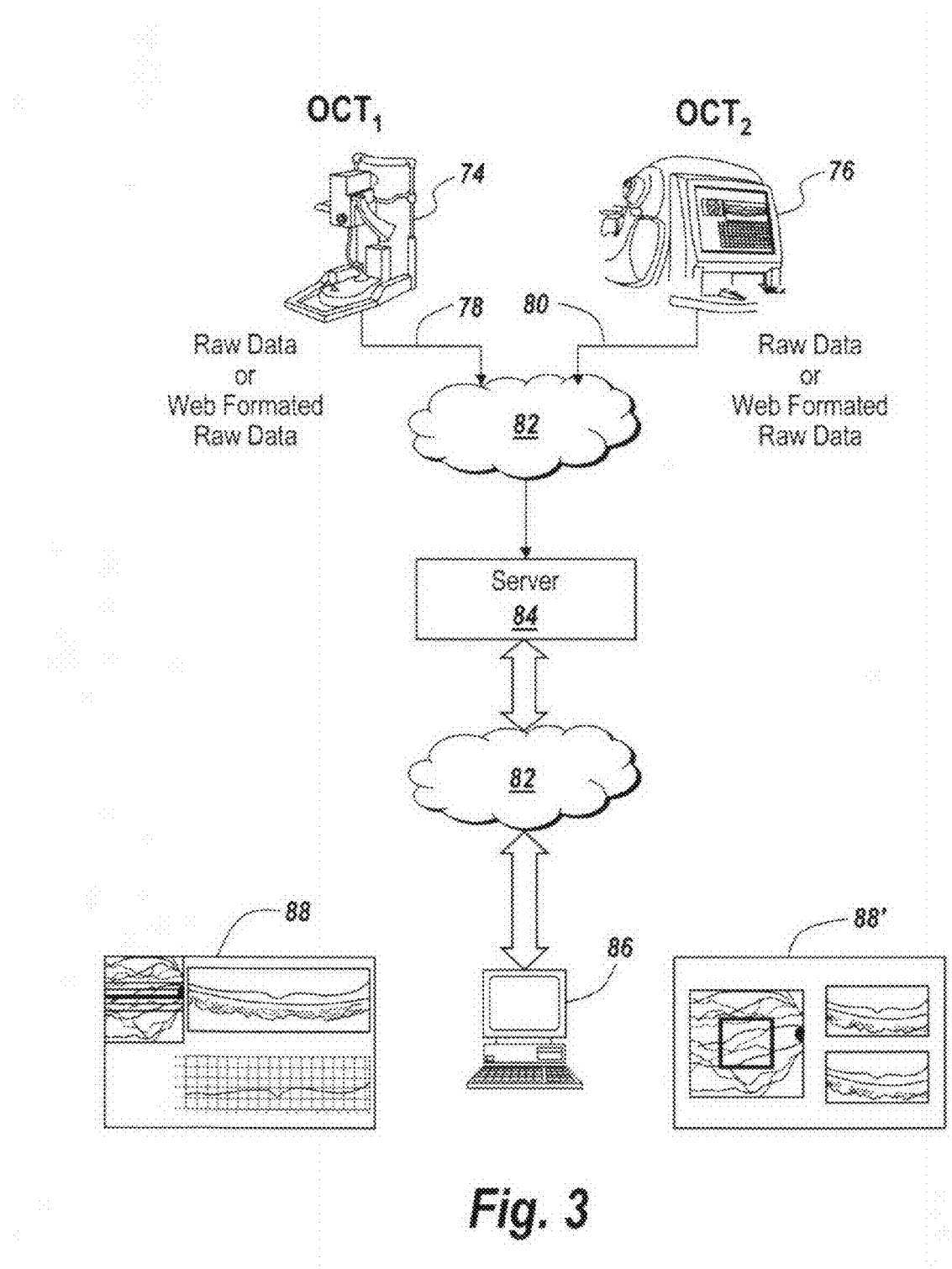
FIG. 3 is a diagrammatic illustration of the utilization of two different OCT devices from separate manufacturers providing raw data or web formatted data to a server that distributes the data to a remote viewing device such as a personal computer where the rendering of exam results and the remote manipulation of data is performed.

Referring to FIG. 3, assuming that one has an $OCT_1$ device 74 manufactured by one manufacturer, and an $OCT_2$ device 76 manufactured by another manufacturer; and further assuming that each of these devices can output either raw data or web formatted raw data on respective links 78 and 80 across the web 82 to server 84, then, when queried from a remote web enabled device 86 over the internet 82 to server 84 a display 88 at the web enabled device 86 can be made to display either that which is originally presented by for instance the first OCT device, or in a different format as shown at 88[1] what would be available from a second OCT device manufactured by another manufacturer.

In short, since all of the raw data is stored at server 84 and since this data may be manipulated to provide various screens under the control of the web enabled device, then it is possible to display at the remote location either the format of the original machine, or the format of another machine.

What will be appreciated is that if an ophthalmic office has a number of different machines and a number of different doctors, then if a doctor wishes to see the results of an OCT exam remotely he can do so either by utilizing the format associated with the machine on which the exam was performed or can alternatively select the format of a different machine. Thus, the subject system can convert the raw data from one machine format to another machine format under the remote control of the practitioner so that the practitioner can view the results of the OCT exam in a format that he or she is familiar with, regardless of the type of machine that actually performed the exam.

Figure 4:
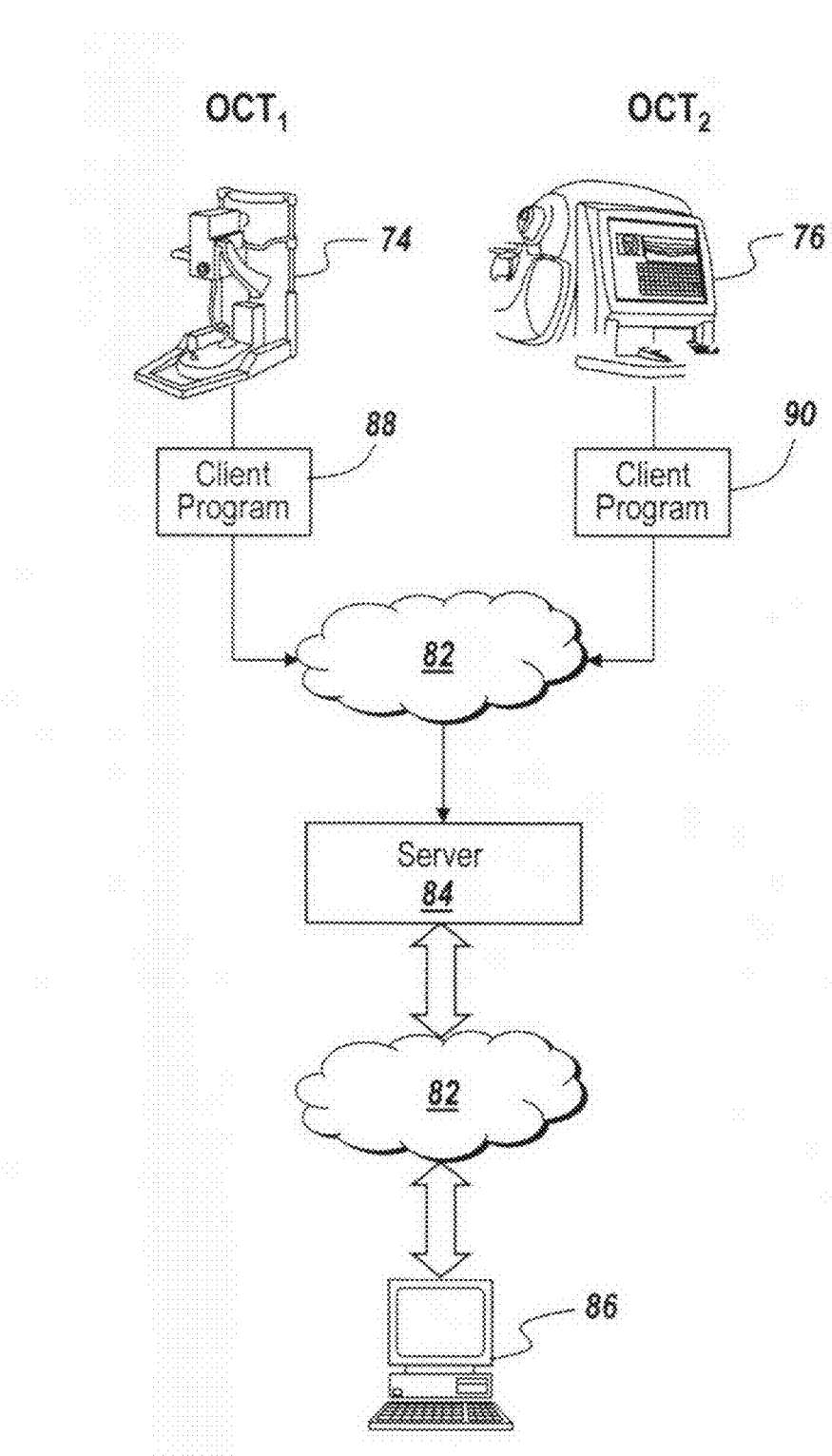
FIG. 4 is a diagrammatic illustration of the same type of system as illustrated in FIG. 3 in which two different machines are provided each with a client program to extract the associated raw data.

Referring to FIG. 4, in which identical units have like reference characters, it can be seen that if the output of a particular OCT machine is not web enabled, the machine may be provided with a specialized client program 88 or 90 so that the raw data can be extracted from the machine and may be processed or converted prior to its being uploaded onto server 84.

Figure 5:
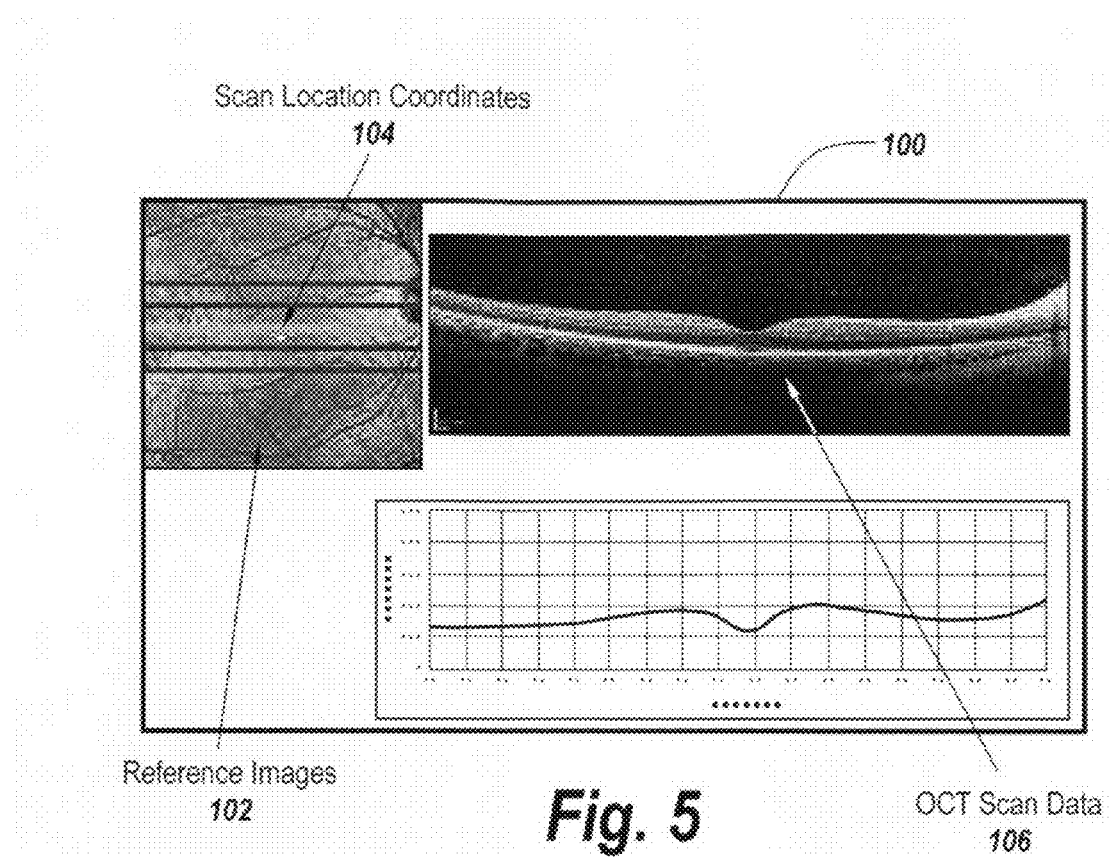
FIG. 5 is a screen shot of the output of an OCT device illustrating scan location coordinates, a reference image, OCT scan data and scale factors.

Referring to FIG. 5, as discussed, some core data components of an OCT exam are common across all OCT device manufacturers. For instance as illustrated at 100 a reference image 102 is shown which is utilized by practitioners to be able to reference OCT data to an image of an eye that has either previously been taken, or has been constructed from the OCT scan data. As illustrated at 104 scan location coordinates may be placed on top of the reference image, with these coordinates defining the location of the OCT scans themselves.

Note that the reference image may be a forward facing view of the eye surface, being imaged either posteriorly or anteriorly, with this image having been generated conventionally to provide the user with a normal looking view so that the locations of the OCT scans can be seen as they correlate to the surface of the eye.

Display 100 can also display scan data as illustrated at 106 which shows cross-sectional scans of a retina to display tissue layers of the segment of the eye being imaged.

Figure 6:
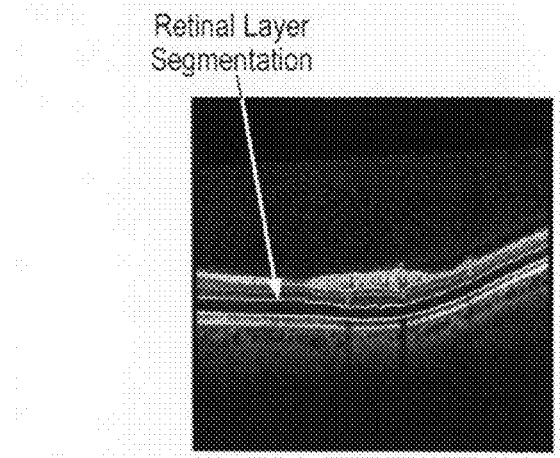
FIG. 6 is a screen shot of retinal layer segmentation.

Referring to FIG. 6, the core data from virtually every OCT instrument or device includes segmentation data obtained from automatic image processing routines that analyze the OCT scans and outline various anatomic structures such as the layers of the retina, layers of the cornea, the iris, the lens, the optic nerve head, etc. It is the segmentation data which may be called up from the remote location.

For instance as shown in FIG. 6 a retinal layer segmentation can be called up which is the result of analysis that defines the layers of the retina.

Figure 7:
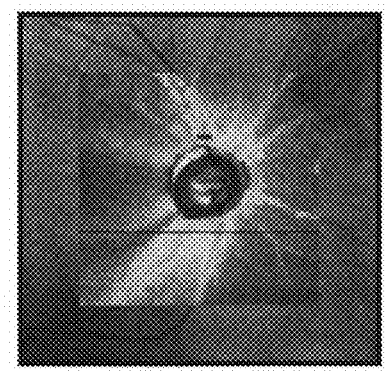
FIG. 7 is a screen shot of a front view of the retina with a thickness topographic map overlaid on top.

As illustrated in FIG. 7 another view of the retina is shown, in which thickness values are derived from the segmentation layers and plotted as a topography map, using a color scale to indicate the thickness of the retina where the OCT scan was performed.

Figure 8:
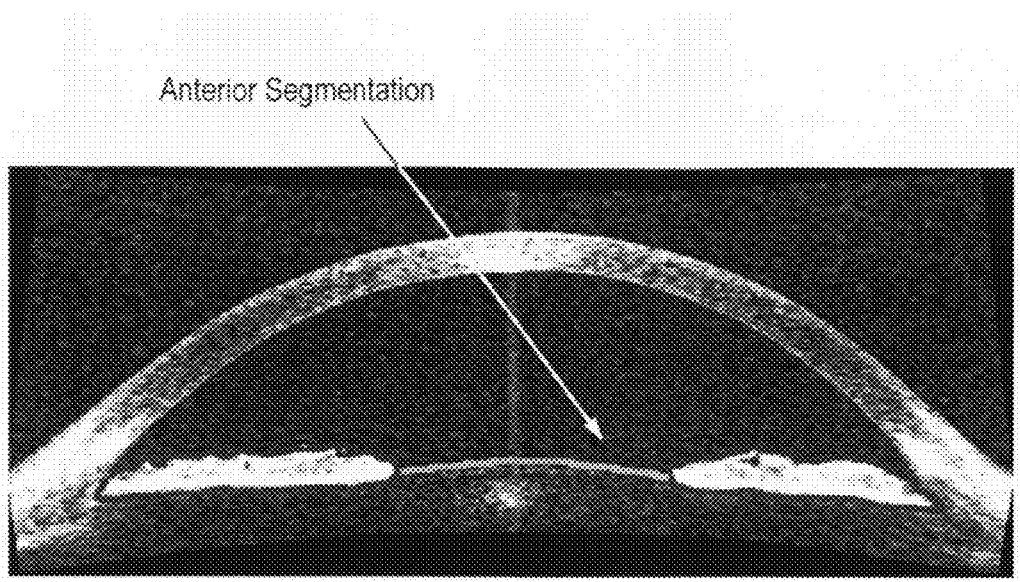
FIG. 8 is a screen shot of the anterior segment of the eye with various structures segmented.

Referring to FIG. 8, another type of segmentation that may be called up from a remote location is from the anterior segmentation of the eye. These are the result of analysis that defines structures in the anterior segment of the eye, such as the iris, the anterior and posterior lens surfaces and the cornea.

Figure 9:
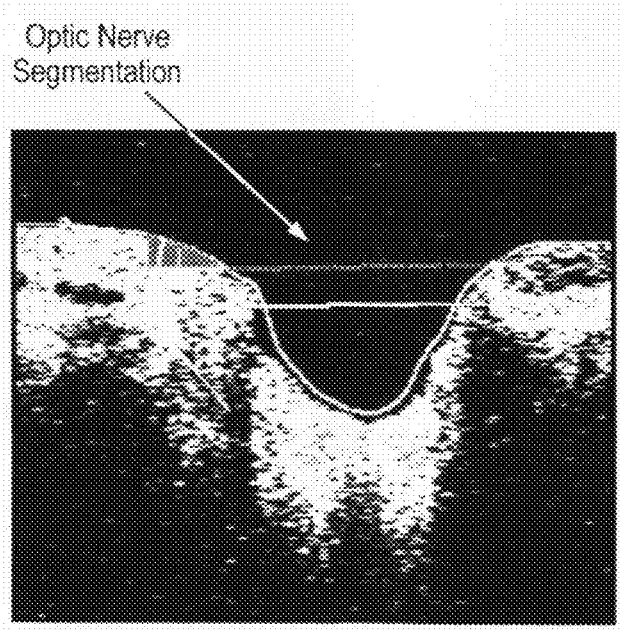
FIG. 9 is a screen shot of optic nerve segmentation of an OCT scan.

Also core data which can be called up is the optic nerve segmentation as shown in FIG. 9 that is a result of an analysis that defines the shape and cupping of the optic nerve.

Figure 10:
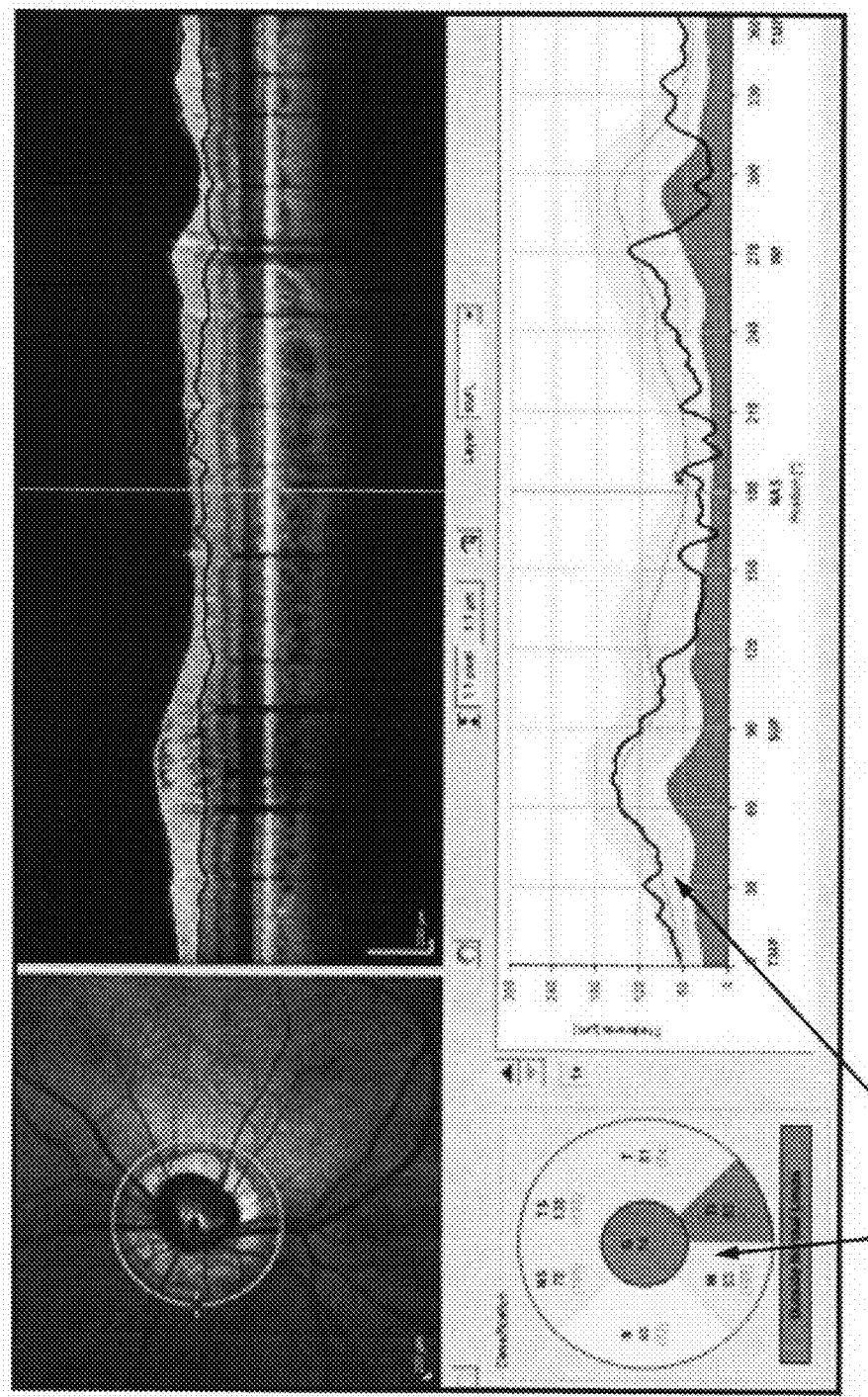
FIG. 10 is a screen shot showing the display of normative data.

Finally as illustrated in FIG. 10, the core data components from an exam from an OCT device as illustrated in FIG. 10 may include normative data provided by many OCT device manufacturers who have compiled normative databases which for instance correlate the thickness results of a retina layer segmentation around the optic nerve to a database of a wide variety of patient samplings to determine if the results are normal or suggestive of a disease.

These presentations are oftentimes available on the machine display itself and by virtue of the subject invention may be called up remotely so that the practitioner may readily view that which he would normally view if he were in the same room and viewing the exam data from the original machine.

It will be appreciated that the practitioner at a remote location may wish to compare exam data from two different machines or data from the same subject taken at different times. The server data may be manipulated to present for instance the results of an exam at one time and then compare in a screen directly underneath the original screen the results for an exam at a later time. Moreover, the subject system may provide the exam results from the machine of one manufacturer and then compare the results to the results from a machine from a second manufacturer, in both instances presented to the remote user by screens that are one on top of the other or side by side so that the practitioner can make the comparison. Additionally, the results of layer segmentation can be subtracted from multiple exam dates to show the change in thickness of the tissue layer from one exam to the next. This change can be represented as a topography map showing the change values as a color overlay.

Figure 11:
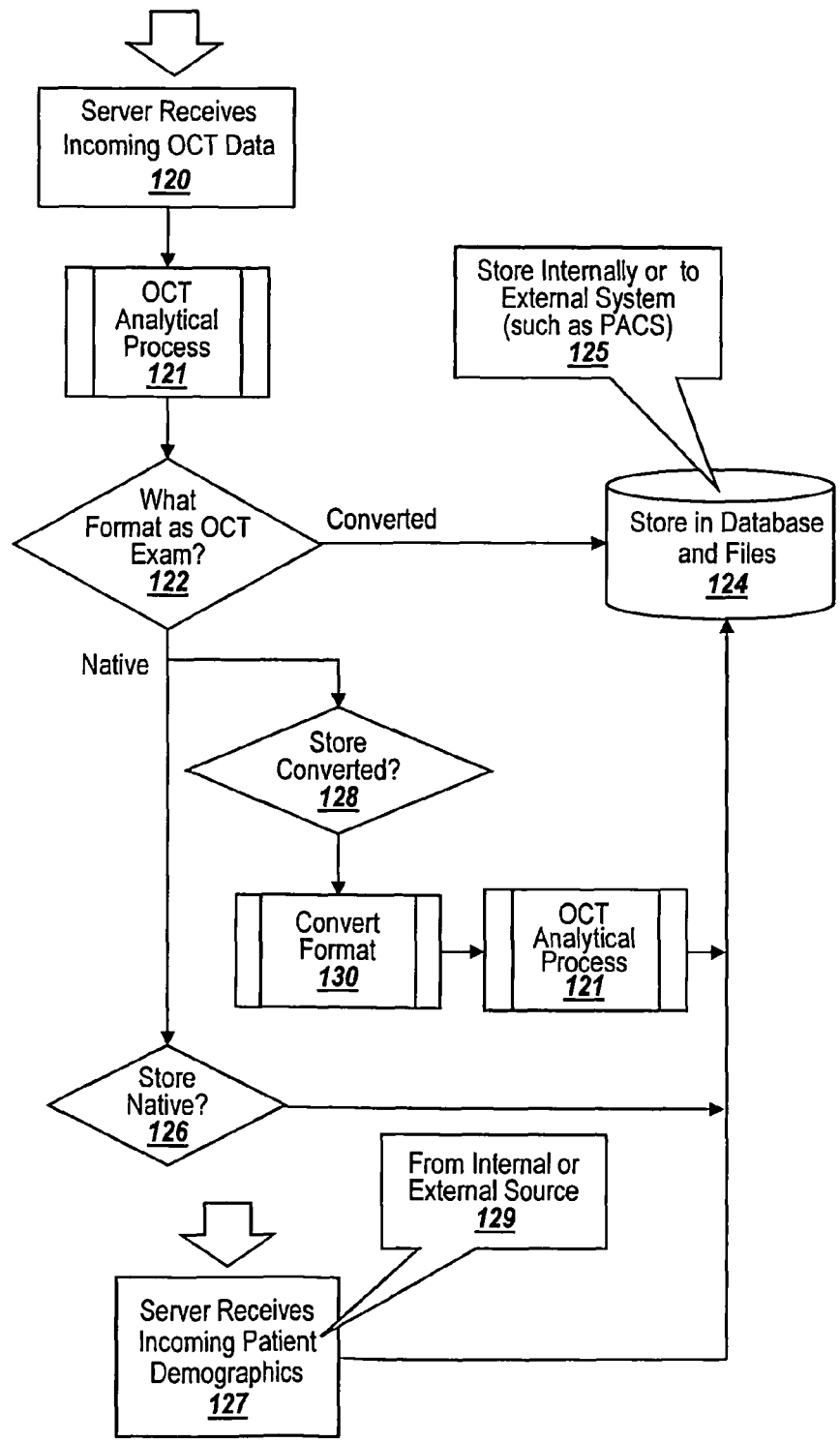
FIG. 11 is a flowchart showing the import service in which a server receives incoming OCT data, stores it and offers various processing subroutines for handling multiple formats of OCT data, as well as an array of conversion and analysis routines.

Referring now to FIG. 11, for import services a flowchart illustrates at 120 that the server receives incoming OCT data which is coupled to the ability to run any of the OCT analytical subroutines 121, followed by a decision block 122 that permits a path forward depending upon what format the incoming OCT exam is in. If it is already converted to a web-enabled format, it may store that format in a database as illustrated at 124. On the other hand if the format is a native format the option to store the native format is illustrated at 126, whereas the option to store in a web format is illustrated at 128. If the web format is selected, then the native data is converted to the web format as illustrated at 130, and the option 121 to provide any OCT Analytical subroutines is again available prior to being stored in the database 124. It should be noted that either or both formats can be stored. It should also be noted that comment 125 shows that the storage of the engine does not have to reside on the server itself, but rather can be an external archival system, such as PACS. In addition to receiving incoming OCT data, the import service can also receive incoming patient demographic data 127 and store it in the associated database and files to eliminate the need for users to type in the patient demographic data to start an exam. Comment 129 also shows that this demographic data can come from a data source internal to the engine, or from another source that can supply that information, such as a PACS system or electronic medical records.

Thus it will be appreciated that this import service is extremely flexible and can handle OCT data in any number of configurations and adapt its processing pipeline accordingly.

Figure 13:
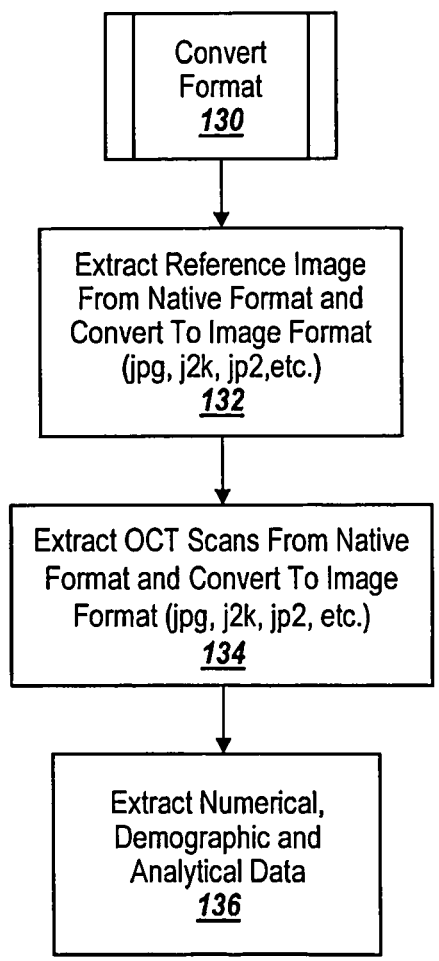
FIG. 13 is a flowchart of the Convert Format subroutine, which extracts the OCT core data components from the native format, such as reference images, B-scans and numerical data, and converts them into useable types that can be handled for processing and display.

FIG. 13 shows the Convert Format subroutine, which is used to convert the OCT exam data to the web format as illustrated in 130. One may seek to extract a reference image from the native format and convert it to an image format as illustrated at 132, with the image format being any type that suits the application and provides the flexibility required to achieve good quality compression for short transmission times while not sacrificing image quality. Such an example would be jpeg, j2k, jp2 or other format. The conversion to the web format may also include the extraction of the OCT scans from the native format and converting to an image format as illustrated at 134, whereas the conversion to the web format may involve the extraction of numerical, demographic or analytical data and conversion to a web format such as XML as illustrated at 136.

This subroutine is available to numerous services on the client, server and viewer applications.

Figure 12:
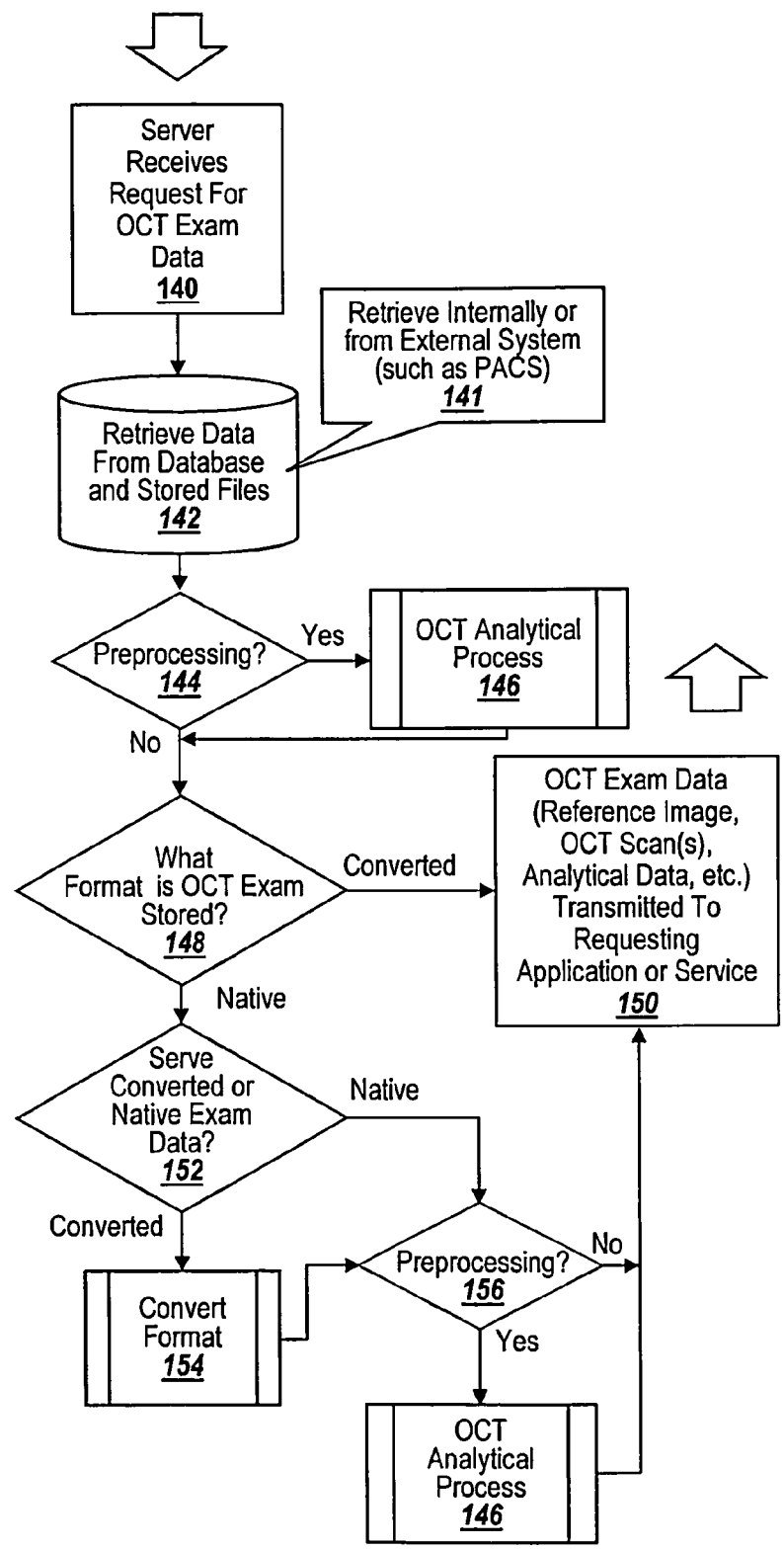
FIG. 12 is a flowchart showing the retrieval of data from the storage associated with the server of FIG. 11, indicating the handling of the format, whether native or web, appropriate conversions and preprocessing so that the reference image, OCT scans, analytical data and the like are transmitted to the requesting application via the web.

Referring now to FIG. 12, the exam data retrieve service is illustrated at 140 in which the server receives a request for OCT exam data. As illustrated at 142 the data is retrieved from the database and stored files, at which point there is a decision to be made as to whether preprocessing is needed, as illustrated at 144. If preprocessing is needed, OCT analytical process subroutines are performed at 146. It should be noted that Comment 141 shows that the exam data retrieved can either be from the engine's database, or from an external source, such as a PACS system.

If no preprocessing is involved then there is a decision made at 148 as to what format the OCT exam is stored in. If it is the web format then as illustrated at 150 reference image, OCT scans, analytic data and the like are transmitted to the requesting application via the web.

On the other hand if the OCT exam is stored in the native form as illustrated at 152 a decision is made whether to deliver it to the requesting application in the native form and supply it to process 150, thus delivering the native raw exam in its original format, or whether to convert it into a web format as illustrated at 154, at which point there is a preprocessing decision made as illustrated at 156. If the decision is no, then the unpreprocessed web formatted data is coupled to process 150. On the other hand, if preprocessing is required, OCT analytical process 146 is invoked that performs the preprocessing and then sends the preprocessed web data to process 150. It should be noted that both the native and web converted formats pass through the preprocessing decision 156 before being delivered and transmitted through 150.

Thus it will be appreciated that the stored data may be pushed out to the remote user in any one of a number of preprocessed, converted or native forms which have been selected by the practitioner.

Figure 14:
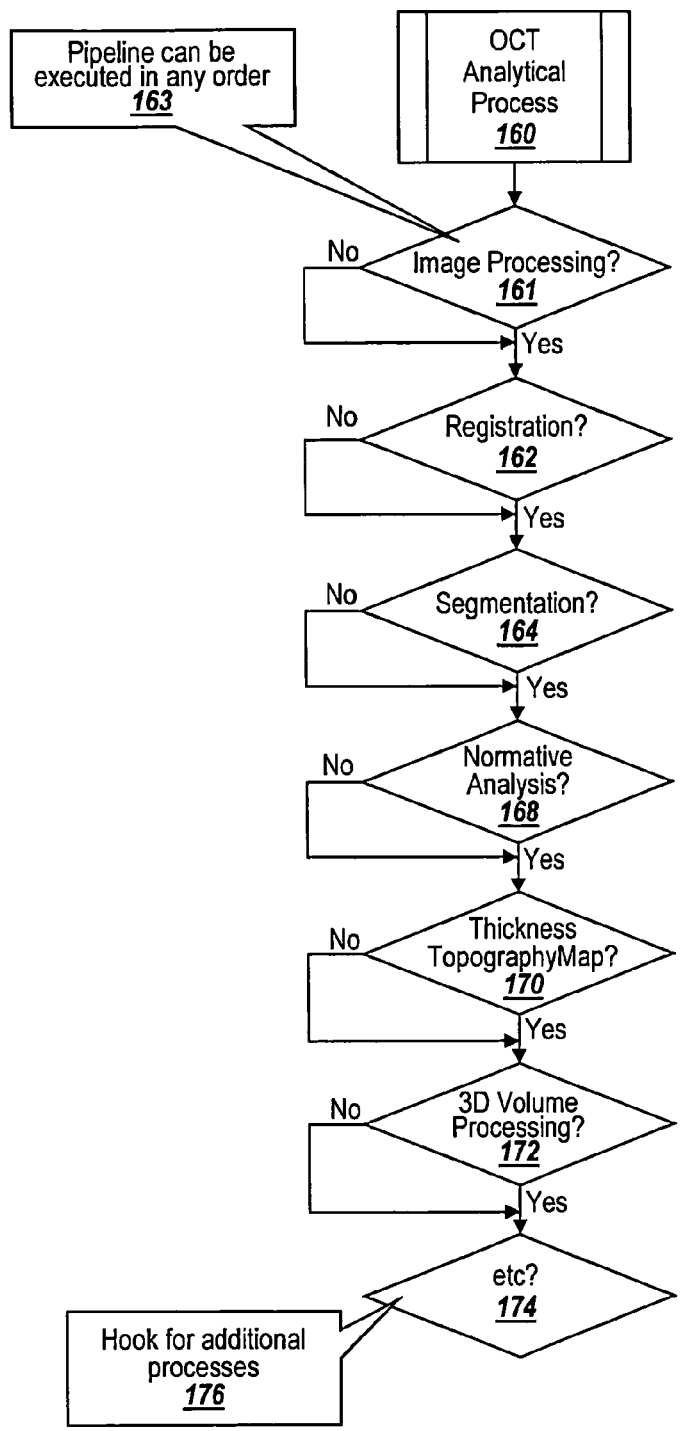
FIG. 14 is a flowchart of the OCT Analytical Process subroutine, which includes several routines for processing the numerical data, such as image processing, registration to align the scans, segmentation to recognize tissue layers, normative data analysis, generation of thickness topography data, generating 3D volume datasets, and hooks for additional routines that can be added at any time.

Referring now to FIG. 14, a flowchart of the OCT Analytical Process subroutine is shown. In this routine, any number of analysis or processing can be performed on the OCT data. For example, image processing 161 can be used to remove noise from an OCT scan or enhance the contrast, Registration 162 can be used to correct for motion during a volume scan, or align volume scans from two different dates for the same patient for comparison. Segmentation 164 can be used to run segmentation algorithms to detect layers of the retina, Normative Analysis 168 can be used to determine the likelihood of a patient's nerve fiber layer thickness indicating glaucoma. Thickness Topography Map 170 can generate a topographic overlay for OCT data indicating the thickness of the patient's retina. 3D volume 172 can be used to generate a 3D volume for display from a cube of OCT B-scans. There are also empty place holders 174 for new algorithms to be inserted that may be specific to one device or another indicated by comment 176. It should be noted as in comment 163 that the subroutines in this pipeline can be run in any order, or as many or as few as are needed or desired.

It will be appreciated that this is a highly flexible subroutine to allow for all of the necessary processing flexibility needed for OCT exam data, and is also available to all parts of the engine, from client, server and viewer applications.

Figure 15:
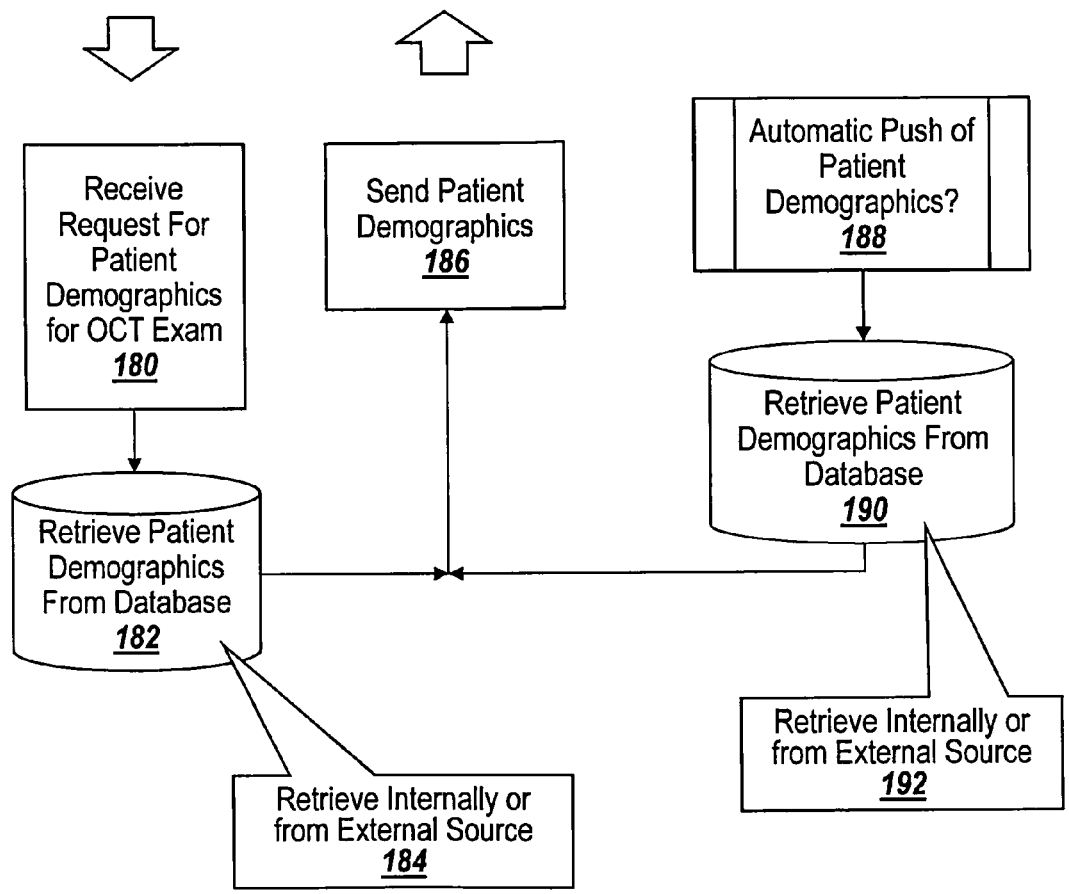
FIG. 15 is a flowchart of the Server Export Service which can access and distribute patient demographics to OCT devices via the web to prevent the technician from having to enter patient data at the beginning of each exam.

Referring now to FIG. 15, the Server Export Service flowchart is shown receiving a request for patient demographics at 180, and then retrieving the requested demographics at 182. It will be noted that comment 184 shows that the demographics can be retrieved from the engine's database, or from an external source such as a PACS system or electronic medical records. From there, the demographic data is supplied back to the requesting application. It should also be noted, there is another variant 188 of this service which can push demographics automatically, as they are available from 190 and also from the engines data or from an external source, as per comment 192.

It will be appreciated that this is a very flexible and adaptable configuration to supply the OCT devices with the demographic information for their patients so they do not have to enter the information manually, as well as avoiding potential errors with human data entry.

Figure 16:
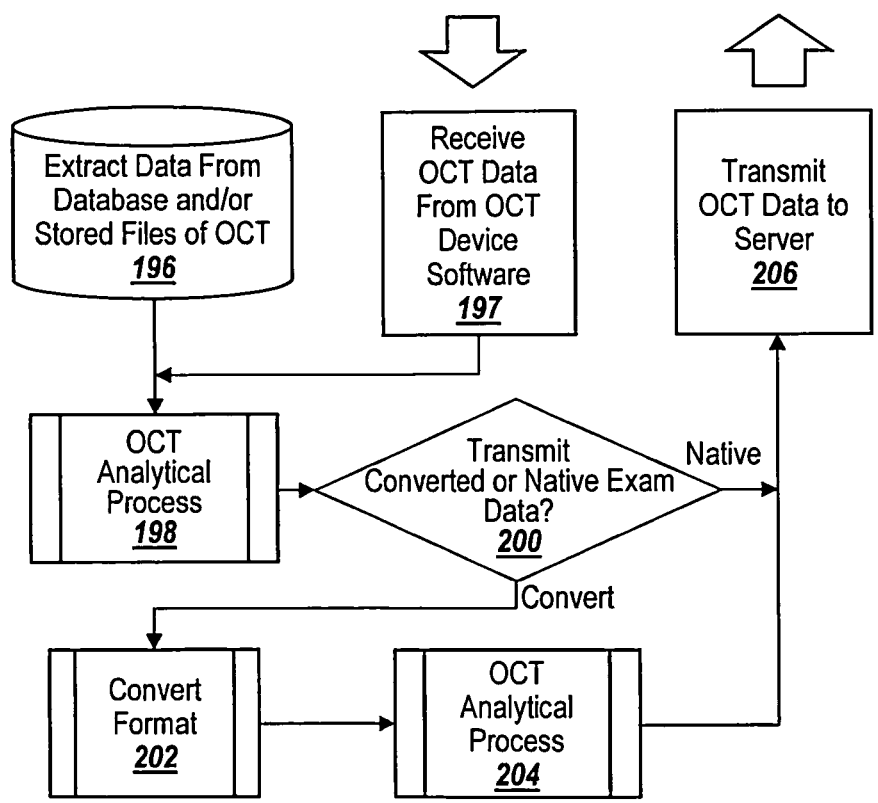
FIG. 16 is a flowchart of the OCT Exam Extraction service that is part of the client program which extracts OCT data from the device and transmits it to the server on the web.

Referring now to FIG. 16, a flowchart is shown for the OCT Exam Extraction service, which is used to send and receive OCT exam data to the server. In the absence of any available routines to output the raw data from the OCT device software, the process begins at 196 by extracting raw data from the OCTs database and stored files. If the routines do exist, then the exported data is received by this service and enters the same pipeline into 198, which is a decision as to whether or not any OCT Analytics are required from the processing pipeline. After that, a decision 200 is made whether or not to send the exam to the server in a web converted or native format. If not, the data is sent out to the server on 206. If conversion is required, then a Convert Format subroutine 202 is called, and then another opportunity to run an OCT Analytical process 204 is available before sending it to the server on 206.

It will be appreciated that this extraction service is a flexible system that can be adapted to any OCT and transmit the exam data in a wide variety of formats to meet any requirements.

Figure 17:
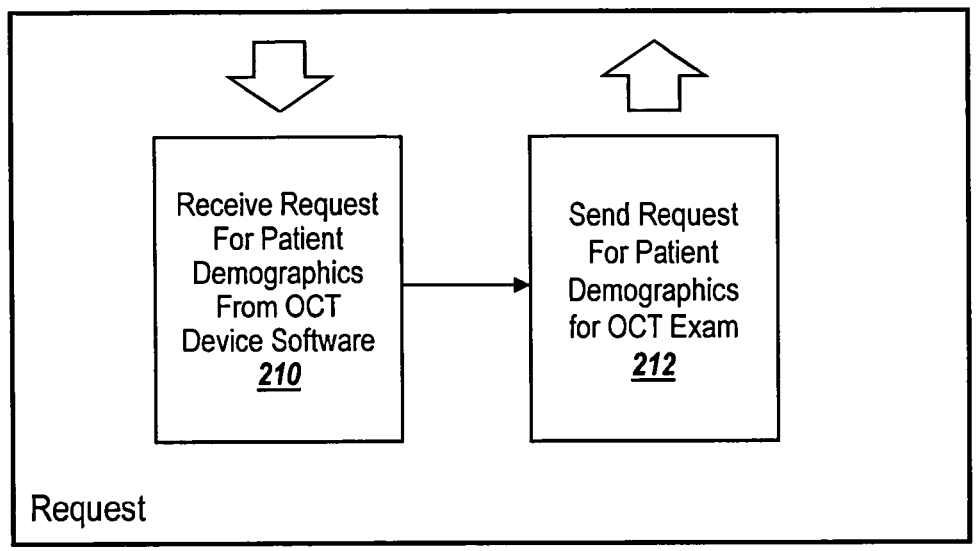
FIG. 17 is a flowchart of the OCT Patient Demographics Retrieval service which engages in bidirectional communication to retrieve the demographics for a patient from the server via the web and provide it to the OCT device directly.
Figure 17:
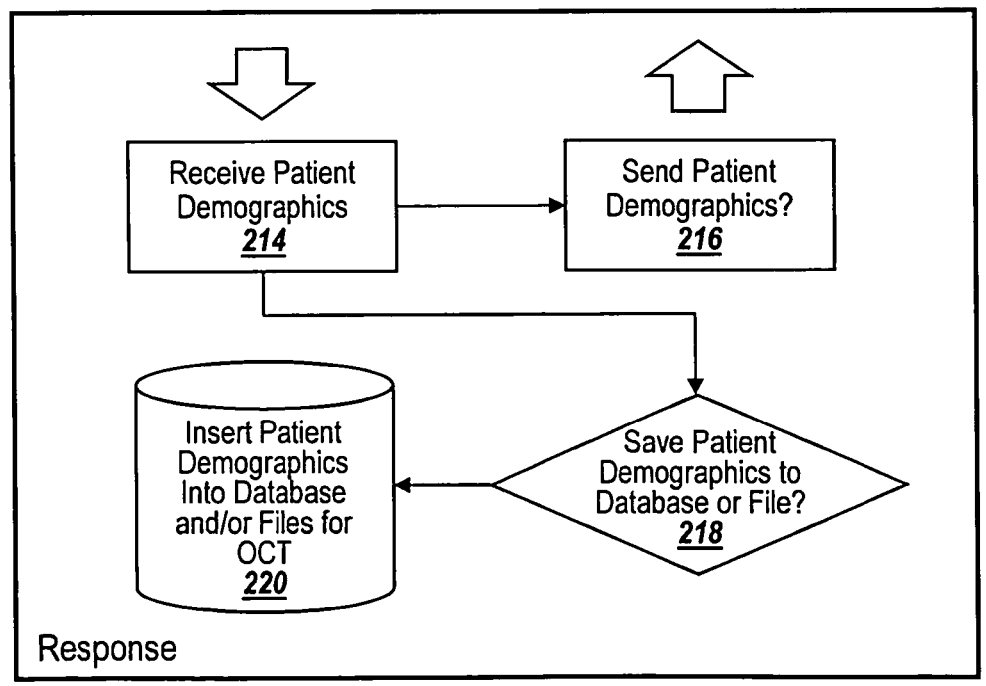

Referring now to FIG. 17, a flowchart for the OCT Patient Demographics Retrieval Service is shown. This service acts as a conduit to route communication for this information across the web, rather than just the local area network. OCT systems making requests for demographics are received in 210 and then routed to the web server via 212. Responses containing the demographic information from the server are received from the web on 214, and passed to the requestor on the local network via 216. A decision block 218 provides the ability to insert the demographics directly into the OCTs database 220 if it is desired and the ability to do so exists.

It will be appreciated that this conduit provides wide area network communication for a local area network feature, thus simplifying the infrastructure and reducing the cost.

Figure 18:
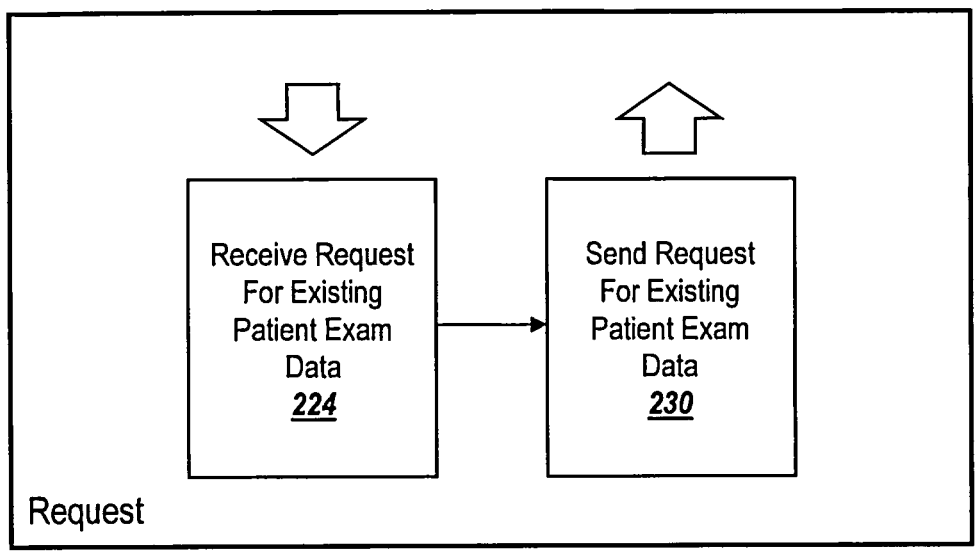
FIG. 18 is a flowchart of the OCT Patient Exam Retrieval service which engages in bidirectional communication with the server to receive existing exams from the web and route them to the OCT device directly.
Figure 18:
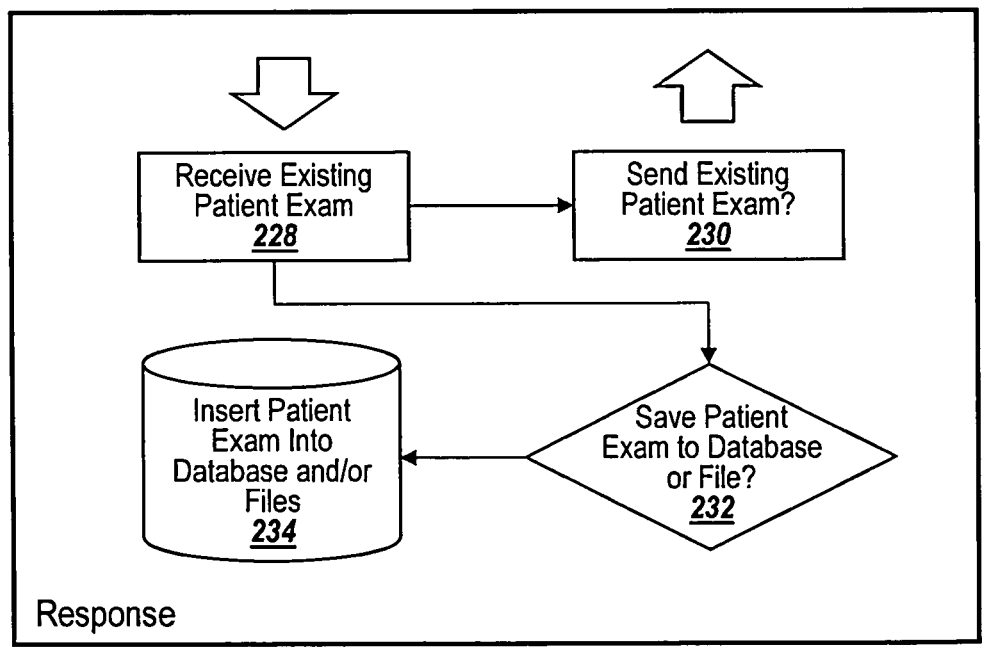

Moving on to FIG. 18, a flow chart of the OCT Patient Exam Retrieval Service is shown. This is a similar conduit to that shown in FIG. 17, but passes an OCT exam rather than patient demographics. OCT systems making requests for an existing patient exam are received on 224 and routed to the server on 226. Responses containing the data are received from the web on 228, passed on to the requestor via 230, with a decision block 232 to save it directly to the OCT machine 234 if it is desired and the ability to do so exists.

It will be appreciated that this conduit provides wide area network communication for a local area network feature, thus simplifying the infrastructure and reducing the cost.

Figure 19:
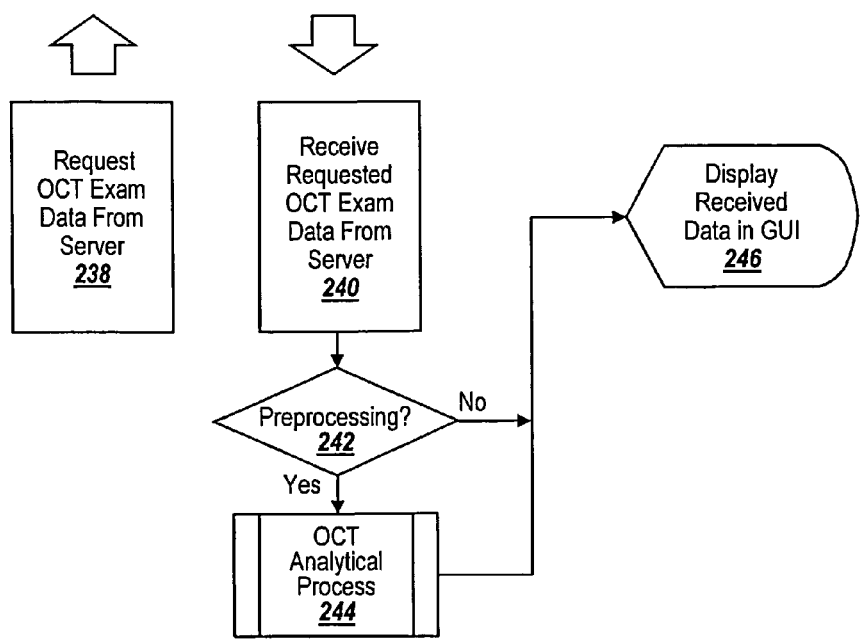
FIG. 19 is a web browser/mobile application flowchart indicating the request of OCT exam data from an associated web server and the receipt of the requested OCT exam data from the server on a mobile device, as well as the optional processing subroutines and update requests issued by the user through graphical user interface controls
Figure 19:
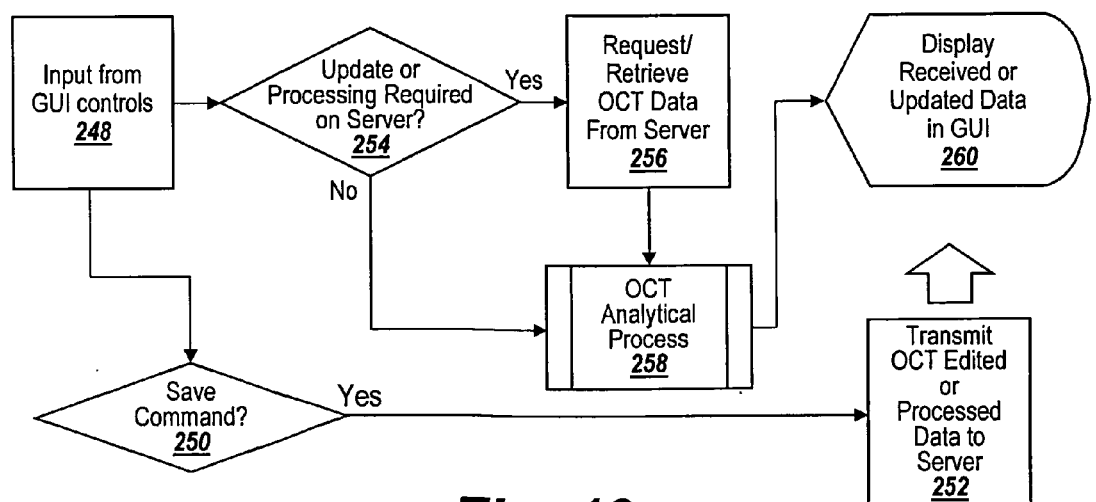

Finally, referring to FIG. 19, for the Web Browser and Mobile Viewer Application as illustrated at 238 there is a request for OCT exam data by the mobile device. The information data that is requested is sent back to the mobile application as illustrated at 240 where the requested OCT exam data is received. Again, if there is no preprocessing involved as illustrated at decision block 242 the results of received data are displayed at 246 using the graphical user interface (GUI) of the web enabled mobile application.

Also, if the preprocessing is required, then the aforementioned OCT analytical process illustrated at 244 is used make sure that the data rendered is in conformity with the requested format from the mobile application.

As the user manipulates the GUI controls 248, the system determines if the user's request requires additional information from the server in order to be fulfilled at 254, for example, the user clicks a button indicating they want to see a thickness topography overlay. If it does not, then it proceeds to the OCT Analytical subroutine at 258 to perform the requested operation that the user asked for, before displaying the data in the GUI screen 260. In the event more data is needed from the server, then a request 256 is made to the server for the necessary information. There is also the capability of issuing a command 250 to save any altered or processed data that the user may have edited or enhanced back to the server so that it can be viewed later.

In summary what is provided is a system for inputting OCT exam data into a server residing on the web which then pushes the information out in a predetermined formatted form to a web enabled device under the control of the web enabled device. Rather than trying to remotely control the original OCT device, in the subject invention the original OCT machine having been instantiated into a global server, with the stored data accessible and manipulatable directly from the remote location without loss of quality and in real time with very little if any latency so that the experience for the practitioner at the remote location will be exactly the same as if he were operating the original OCT device.

It will be appreciated that while the aforementioned examples have been explained in terms of the World Wide Web, this invention is also applicable to any internet or TCP/IP based communication scheme.

It should also be noted that although the web services and figures are described in some specific configurations, they are described as a modular series of building blocks for an engine, and can therefore be configured and mixed and matched in a number of different ways. For example, if an OCT and the server were in the same office, and not only connected by the web, then the Exam Retrieval service or the Patient Demographics service might not be necessary, and the Server Export services might communicate directly to the OCT Import Routines. The invention is intended to be highly modular and capable of being adapted and reconfigured to any scheme desired to operate with the full desired functionality.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. An over-the-Interact-based remote viewing and manipulation system for use with an ophthalmic OCT machine to permit remote viewing and manipulation of the output of said OCT machine on a remote computer, comprising:

an Internet-enabled software engine on a global server, said Internet-enabled software engine instantiating and duplicating the functions of said OCT machine to permit OCT analytic processing including image processing, registration, segmentation, normative analysis, thickness maps, and 3D volume processing, said software engine adapted to be coupled by the internet to the output of said OCT machine utilizing an internet connection scheme to collect, store, retrieve and permit viewing and manipulation of the output of said OCT machine; and a remotely connected viewing and manipulation device coupled by the Internet to said global server and said Internet-enabled OCT machine instantiating software engine for accessing the collected and stored information at said global server in a retrieving step to permit the viewing of the results of an OCT exam from said OCT machine and for manipulating the data that is collected and stored at said global server to enable said OCT analytic processing.

2. The system of claim 1, wherein said Internet-enabled software engine is configurable to output for viewing at a remote location that which is generated by said OCT machine.

3. The system of claim 1, wherein said Internet-enabled software engine is coupled back through the internet to said OCT machine and is operable to remotely control the operation of said OCT machine.

4. The system of claim 1, wherein the output of said OCT machine contains raw binary data, said raw binary data being uploaded to said server using a secure encrypted Internet-enabled client program.

5. The system of claim 4, wherein said server can open upload data, convert it and process it to Internet-capable formats in real time.

6. The system of claim 1, wherein said server can serve collected and stored data to a number of Internet connections upon request, thus to make the results of the OCT machine simultaneously available a number of different remote users.

7. The system of claim 1, wherein said remotely located viewing and manipulation device can manipulate the OCT exam data residing in said server using Internet-enabled devices.

8. The system of claim 7, wherein said Internet-enabled devices include at least one of a computer, an iPad, a tablet and a smart phone.

9. The system of claim 1, wherein said an Internet-enabled software engine duplicates the functionality of said OCT machine.

10. The system of claim 1, wherein said server is remotely readable and manipulatable so as to output data in real time with said engine providing the look and feel of said OCT machine.

11. The system of claim 1, wherein said Internet-enabled software engine includes a bi-directional component such that various types of data relating to OCT exams can be sent back to said OCT machine to eliminate data entry errors and allow further processing of existing exam data.

12. The system of claim 1, wherein said OCT machine develops core data components.

13. The system of claim 12, wherein said core data components include at least one of scan location coordinates, a reference image, OCT scan data, scale factors, segmentation data and normative data.

14. The system of claim 13, wherein said segmentation data includes at least one of retinal layer segmentation data, optic nerve segmentation data and anterior segmentation data.

15. The system of claim 1, wherein said Internet communication includes World Wide Web communications protocols and TCP/IP communications protocols.

16. The system of claim 1, wherein said remotely located viewing and manipulation device includes a display capable of providing comparison views.

17. The system of claim 16, wherein said comparison views include data taken at one time juxtaposed to data taken of another time.

18. A method of providing OCT exam results at locations remote from an OCT machine, comprising the steps of:
  providing a global server having an Internet-enabled software engine coupled to the internet and instantiating the functions of the OCT machine, the server being coupled by the internet to the output of the OCT machine;
  extracting underlying exam data including OCT exam information from the OCT machine and collecting and storing it at the global server in the Internet-enabled software engine coupling a remote viewing and manipulation device by the internet to the global server and the Internet-enabled software engine;
  viewing the results of an exam taken on the OCT machine at the remote viewing and manipulation device by accessing the Internet-enabled software engine and the underlying exam data therefor using the Internet; and,
  manipulating the underlying data stored in the Internet-enabled software engine from the remote viewing and manipulation device.

19. The method of claim 18, wherein the look and feel of the data displayed at the remote viewing and manipulation device is made to match that of the OCT machine.

20. The method of claim 18, wherein more than one OCT machine is coupled by the internet to the global server and wherein the OCT machines operate to manipulate and output common core data, making the Internet-enabled software engine able to service multiple different OCT machines using a universal program.

* * * * *